United States Patent [19]
Jensen et al.

[11] Patent Number: 4,631,413
[45] Date of Patent: Dec. 23, 1986

[54] METHOD FOR QUALITY CONTROL OF PRODUCTS FROM FISH, CATTLE, SWINE AND POULTRY

[75] Inventors: Svend A. K. Jensen, Søborg; Lars Munck, Helsingør; Poul Sigsgaard, Helsinge; Hans H. Huss, Copenhagen, all of Denmark

[73] Assignee: De Forenede Bryggerier A/S, Copenhagen, Denmark

[21] Appl. No.: 618,161

[22] Filed: Jun. 7, 1984

[30] Foreign Application Priority Data

Jun. 13, 1983 [SE] Sweden ................................ 8303327
Aug. 5, 1983 [SE] Sweden ................................ 8304288

[51] Int. Cl.$^4$ ........................................... G01N 21/64
[52] U.S. Cl. ............................. 250/458.1; 250/461.1; 250/461.2
[58] Field of Search ................... 250/372, 458.1, 461.1, 250/461.2; 209/577, 578

[56] References Cited

U.S. PATENT DOCUMENTS 3,449,571 6/1969 Hoerman et al. .
3,497,690 2/1970 Wheeless, Jr. et al. .
4,226,540 10/1980 Barten et al. .
4,421,772 12/1983 Muck et al. .

FOREIGN PATENT DOCUMENTS

B390458 12/1976 Sweden .
2089501 6/1982 United Kingdom .

OTHER PUBLICATIONS

Issue of Federation Proceedings May–Jun. 1966, vol. 25, No. 3, pp. 1016 to 1021, "Some Quantum Aspects of Collagen".
Sunday Times (London) of Apr. 19, 1981.
Meat Trades Journal of May 7, 1981.
Financial Times of May 21, 1981.
Food Manufacture of Jun., 1981.
Food Processing Industry of Jul., 1981.
Meat Trades Journal of Jul. 23, 1981.

Primary Examiner—Janice A. Howell
Attorney, Agent, or Firm—Beveridge, DeGrandi & Weilacher

[57] ABSTRACT

A method for quality control of products from fish, meat, cattle, swine and poultry, for instance for controlling a process for treating or handling such products. The product to be subjected to quality control, or a sample thereof, is exposed to electromagnetic radiation within the range of about 325–360 nm, preferably about 340 nm, and any fluorescent radiation emitted by the product as a result of this irradiation, is analyzed for identifying characteristic fluorescence from biological components in the product or a sample thereof, the presence of such biological components determining the quality of the product. The quality control is carried out in dependence upon the analysis result. Analysis carried out in the wavelength range of about 365–490 nm permits identification of characteristic fluorescence from bones, cartilage, connective tissue and/or fat.

23 Claims, 9 Drawing Figures

METHOD FOR QUALITY CONTROL OF PRODUCTS FROM FISH, CATTLE, SWINE AND POULTRY

BACKGROUND OF THE INVENTION

The present invention relates to a method for quality control of products from fish, cattle, swine and poultry, for instance for controlling a process for treating or handling such products.

The fish processing industry pays great attention to the task of removing the bones from the fish. The removal of bones, e.g. in connection with filleting, is carried out in machines with a subsequent manual trimming for removing any remaining bones which may be observed with the eye or felt by the fingers. Such manual detecting methods are very slow and unreliable, which means that fish products often escape the control with remaining bones undetected. Many fish products which have been boned are delivered in the frozen state in large packages to wholesalers or the canning industry who will also carry out the above-described manual control on a random sample basis for a small part of the package, to assess the presence of any remaining bones in the package. If it is found in this control that the contents of bone exceed a predetermined value, the entire package is discarded, which means a considerable economic loss to the supplier.

In the preparation of meat products by cutting animals and in the making of mixed meat products, such as sausage, brawn, minced meat, pâté etc., both as perishable and canned foods, one has lately placed still higher demands on the declaration of the contents of the products. Analyses in this respect have hitherto been performed substantially on the basis of the chemical constituents of the product, such as fat, protein, ash, water etc., and it has been very time-consuming and difficult, not to say impossible, quantitatively to define the composition of the product on the basis of the animal tissue components which are of great importance for the organoleptic quality, such as tenderness, or the nutritional quality, such as digestibility. It is also evident that the economic values in pure meat are considerably higher than in other animal components, such as fat, connective tissue, cartilage, and that there is thus an economic incitement toward being able accurately to determine the composition of the meat products, so that the raw products can be better utilised in the processing factories. With an accurate method for detecting the most important animal components it would be possible on a large scale to control automatic trimming apparatuses for optimal use of the valuable meat in the animal parts which are difficult to cut manually in a cost-effective way.

One object of the invention is to provide a quick and reliable method for detecting bones in fish products.

Another object of the invention is to provide a quick and reliable method for detecting animal components, such as bone, cartilage, connective tissue, fat and meat (muscles) in meat products, including poultry products, which detection should preferably also allow quantitative determination of at least one of the aforementioned components.

With these objects in mind, the main purpose of the invention is to provide a method for the abovementioned detections which permits a more rapid and at least equally accurate quality control of fish and meat products as compared with prior art methods, for instance for controlling processes for treating and handling fish and meat products.

SUMMARY OF THE INVENTION

According to the invention, these objects are achieved in that the product to be subjected to quality control, or a sample thereof, is exposed to electromagnetic radiation within the range of about 325–360 nm, preferably about 340 nm, that any fluorescent radiation emitted by the product as a result of this irradiation, is analysed for identifying characteristic fluorescence from biological components in the product or a sample thereof, the presence of such biological components determining the quality of the product, and that said quality control is carried out in dependence upon the analysis result.

The invention is based on the surprising discovery that irradiation of fish samples with electromagnetic radiation within the UV range permits detecting bones in the fish sample, and more precisely that irradiation of fish samples at about 340 nm causes a characteristic and visible fluorescence also from a fish bone which is embedded in the flesh of the fish, and further on the surprising discovery that UV irradiation of meat products containing bone, cartilage, connective tissue and fat permits detecting these animal components in the products, and more precisely that the irradiation of animal bone, cartilage, connective tissue and fat with a light of about 340 nm causes a characteristic and visible fluorescence from bone, cartilage, connective tissue and fat, also when the bone is surrounded by meat.

Thus, when a sample of cod fillets with bones were irradiated with electromagnetic radiation at about 340 nm, it was possible with the eye to clearly observe in the sample distinct streaks fluorescing in blue-violet against a light beige background, and in a control the streaks were clearly identified as fish bones and the background as fish flesh. The same colours were obtained when studying this irradiation of fish bone only and of fish flesh only.

It was also possible in this manner to detect fish bones located in fish flesh at a few millimeters' depth.

When irradiating a bone-containing meat sample with electromagnetic radiation of about 340 nm, one could thus visually clearly perceive a deep blue fluoroscent portion against a dark background. In a control, the fluorescent portion was clearly identified as bone and the background as meat.

Similarly, by electromagnetic irradiation at about 340 nm of a cartilage- or connective tissue-containing meat sample, it was possible visually to identify cartilage, connective tissue and meat.

When irradiating a fat-containing meat sample with electromagnetic radiation of about 340 nm, it was further possible visually to clearly perceive a blue and yellow fluoroscent portion against a dark background. In a control, the fluorescent portion could be clearly identified as fat and the background as meat.

As intimated above, the corresponding fluorescence emission characteristics are obtained on a UV irradiation at about 340 nm of pure bone, cartilage, connective tissue, fat and meat samples.

BRIEF DESCRIPTION OF THE DRAWINGS

Reference is now made to the accompanying drawings, in which.

DETAILED DESCRIPTION

A meat or fish product to be subjected to quality control, or a sample thereof, can be exposed to electromagnetic radiation within the range of about 325-360 nm, preferably about 340 nm. Any fluorescent radiation emitted by the product as a result of this irradiation is analyzed for fluorescence that is characteristic of biological components that affect the quality of the product. Analyses can be carried out for emitted radiation in the wavelength range of about 365-490 nm.

The analysis for quality control of fish products can be carried out for emitted radiation in the wavelength range of about 365-450 nm for identification of fluorescence that is characteristic of fish bones. For quality control of meat products from cattle, swine and poultry, the analysis can be carried out for emitted radiation in the wavelength range of about 375-490 nm for identification of fluorescence that is characteristic of bones, cartilage, connective tissue and/or fat.

Figure 1:
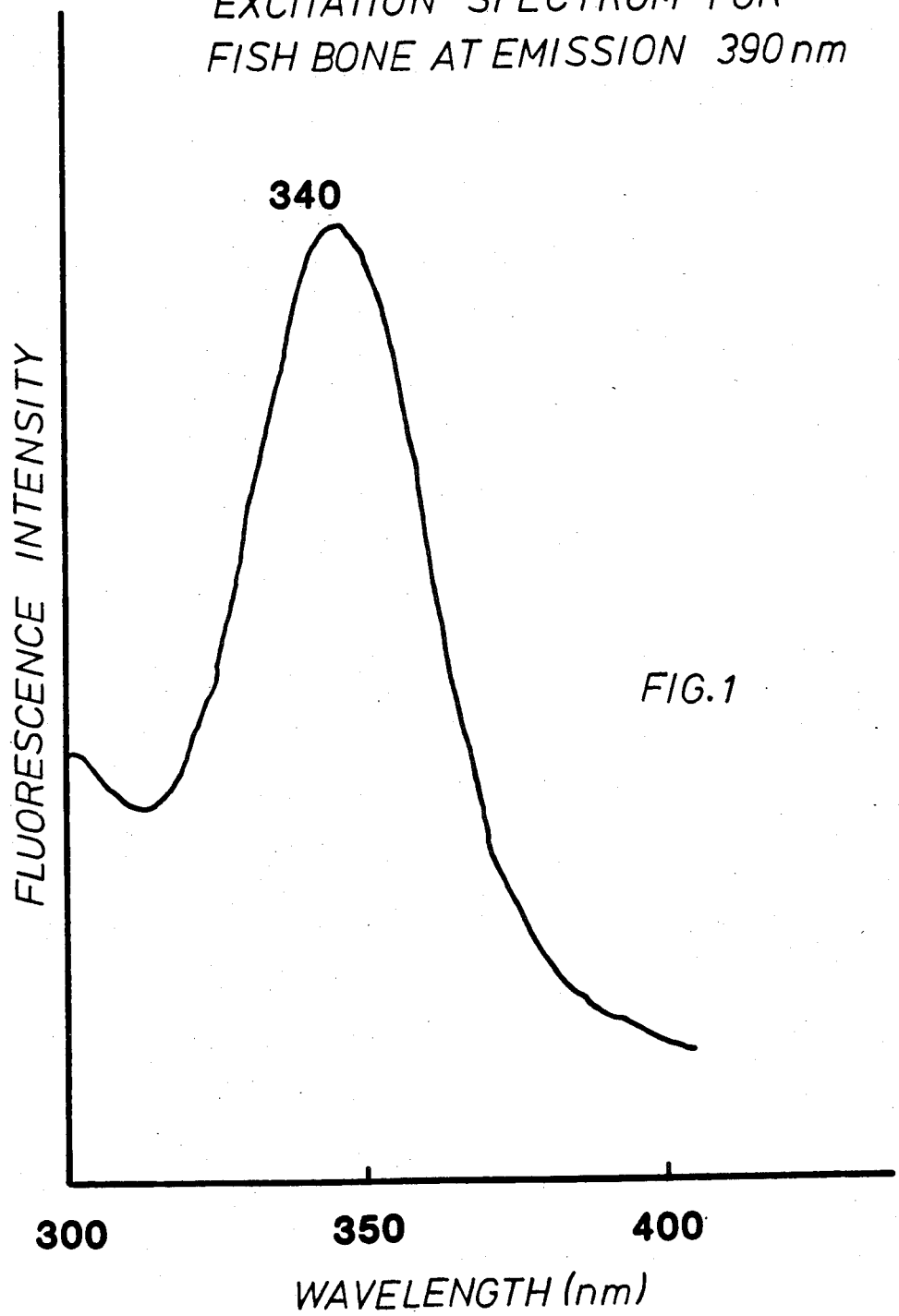
FIG. 1 is an excitation spectrum for fish bone at an emission of 390 nm.
Figure 2:
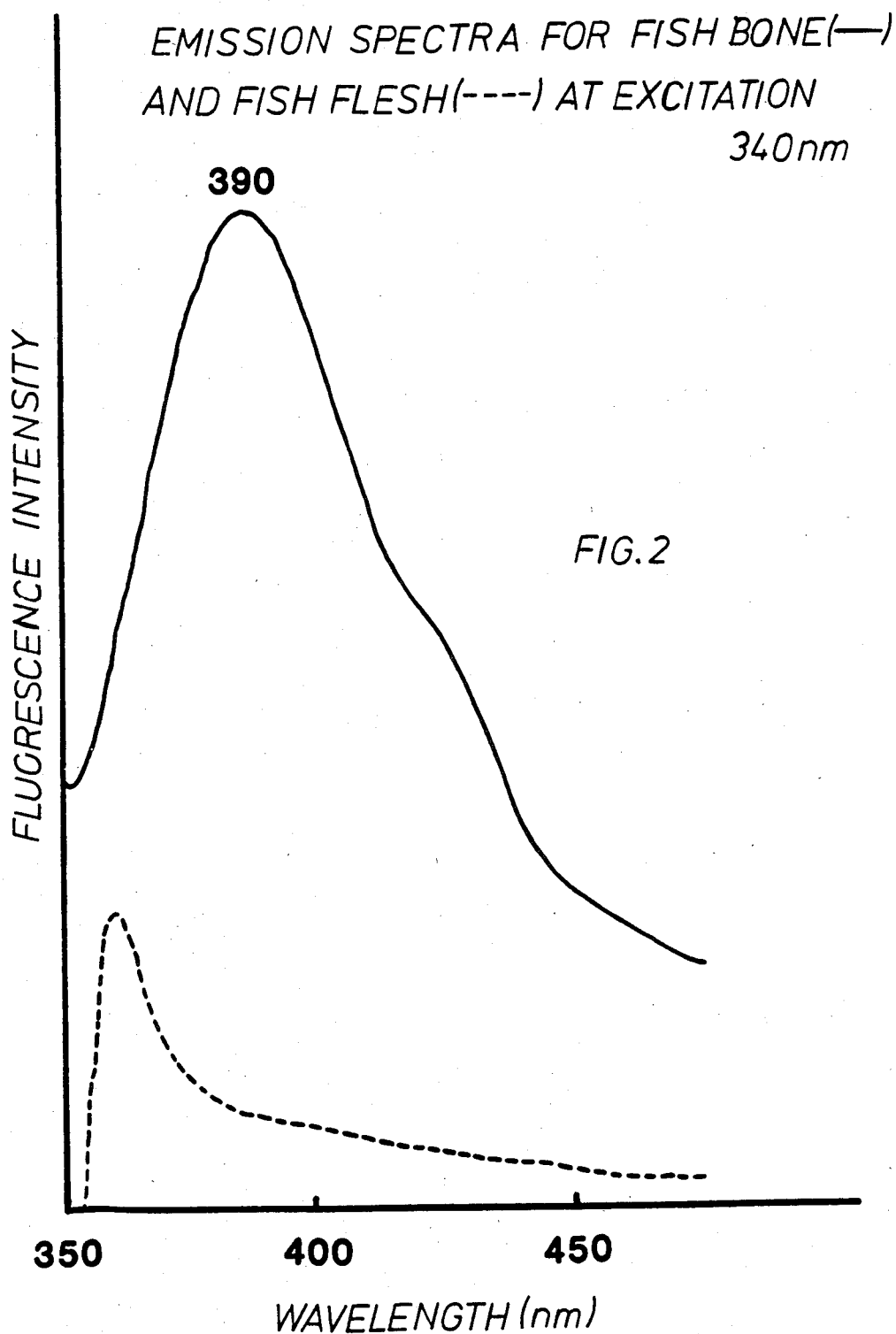
FIG. 2 is an emission spectrum for fish bone and fish flesh at an excitation of 340 nm.

In order to investigate optimum emission and excitation wavelengths for the detection of fish bone, fish bone and fish flesh were studied in a spectrofluorometer. The excitation spectrum of the fish bone had a peak at about 340 nm, the excitation limits being at about 325 nm and about 355 nm, FIG. 1, and the fluorescence emission spectrum at 340 nm excitation had a peak at about 390 nm, FIG. 2. At an irradiation of fish flesh at 340 nm, there was hardly obtained any detectable fluorescence intensity from the flesh. This result is illustrated in FIG. 2 confirming visible fluorescence from fish bone at an irradiation of 340 nm.

It has thus been established that an irradiation of fish parts with electromagnetic radiation within a wavelength range of 325-355 nm unambiguously reveals the presence of any bones by the resulting characteristic fluorescence of the bone.

Figure 3:
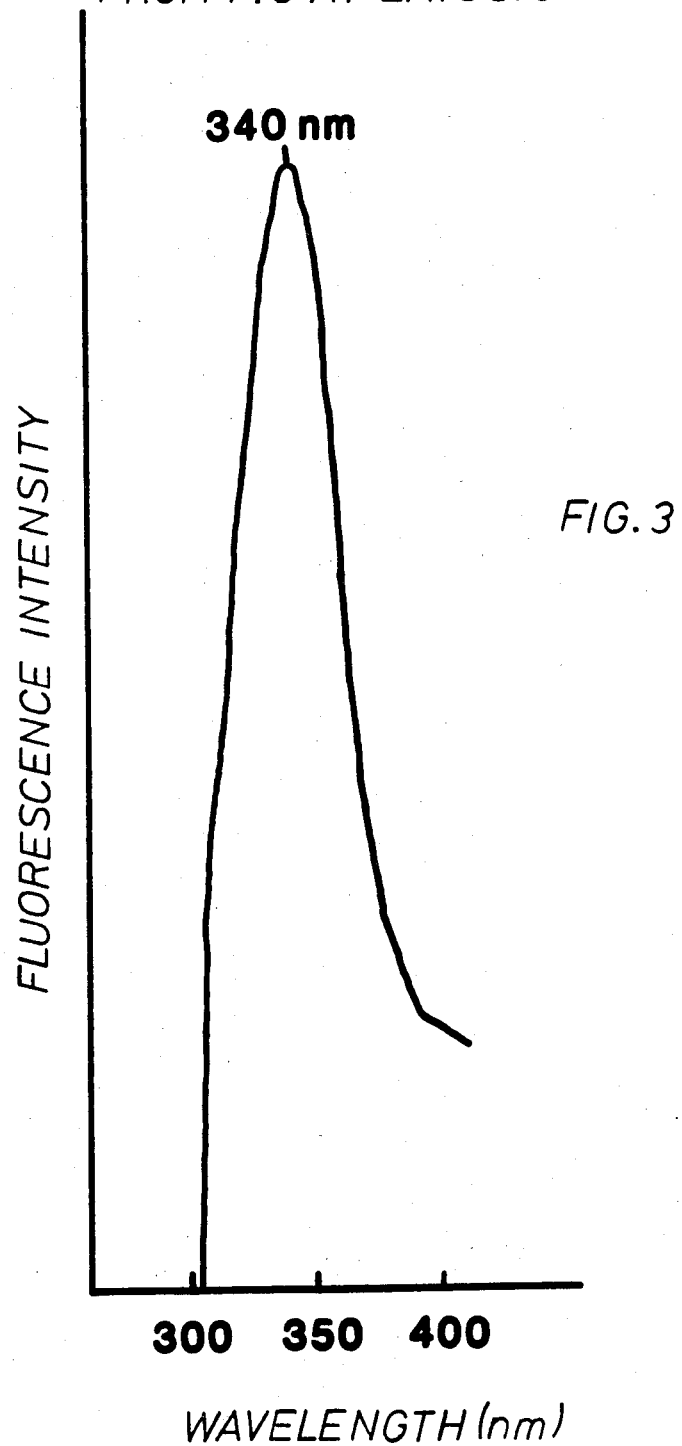
FIG. 3 is an excitation spectrum for cartilage from pig at an emission of 390 nm.
Figure 4:
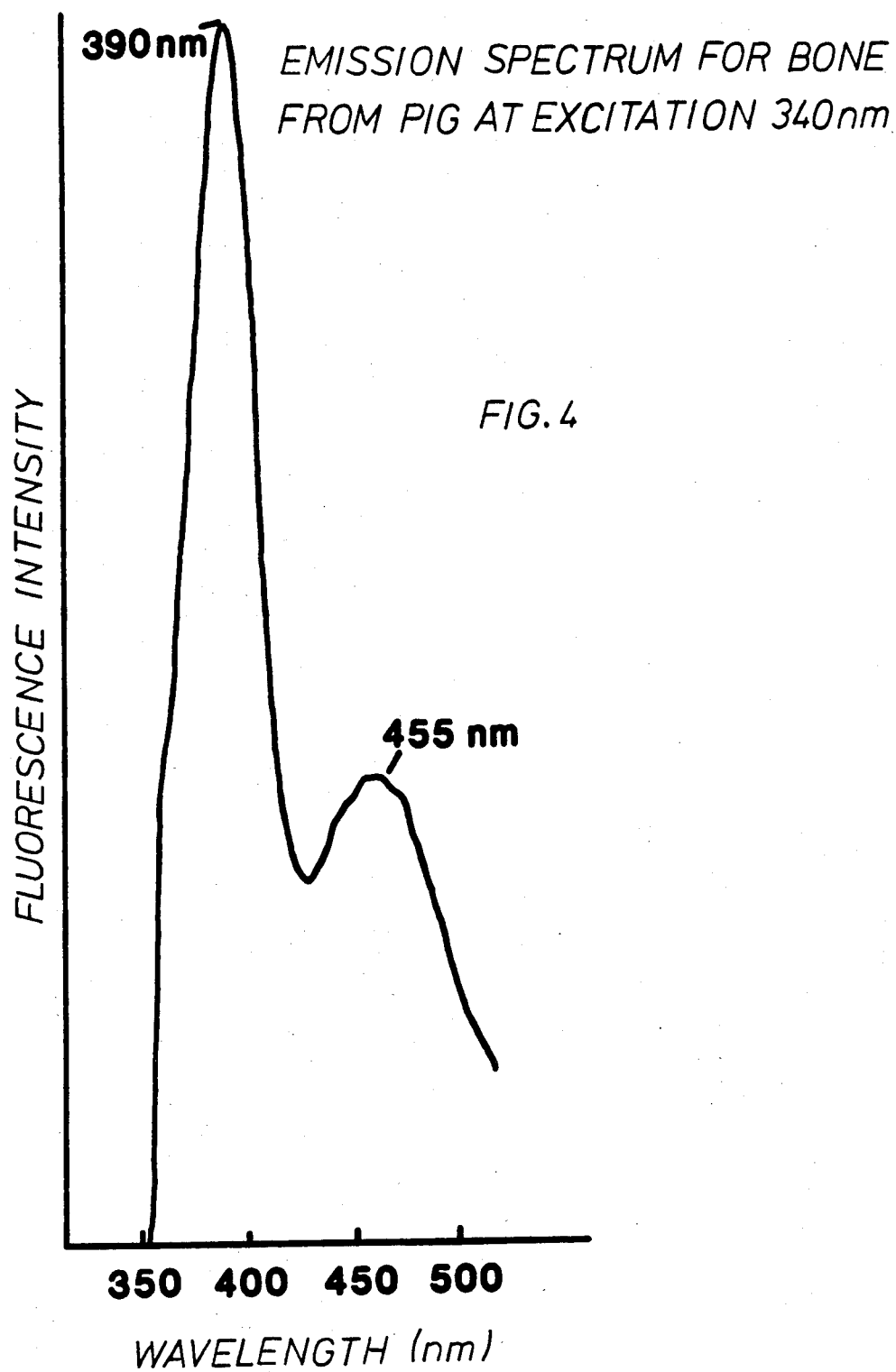
FIG. 4 is an emission spectrum for bone from pig at an excitation of 340 nm.
Figure 5:
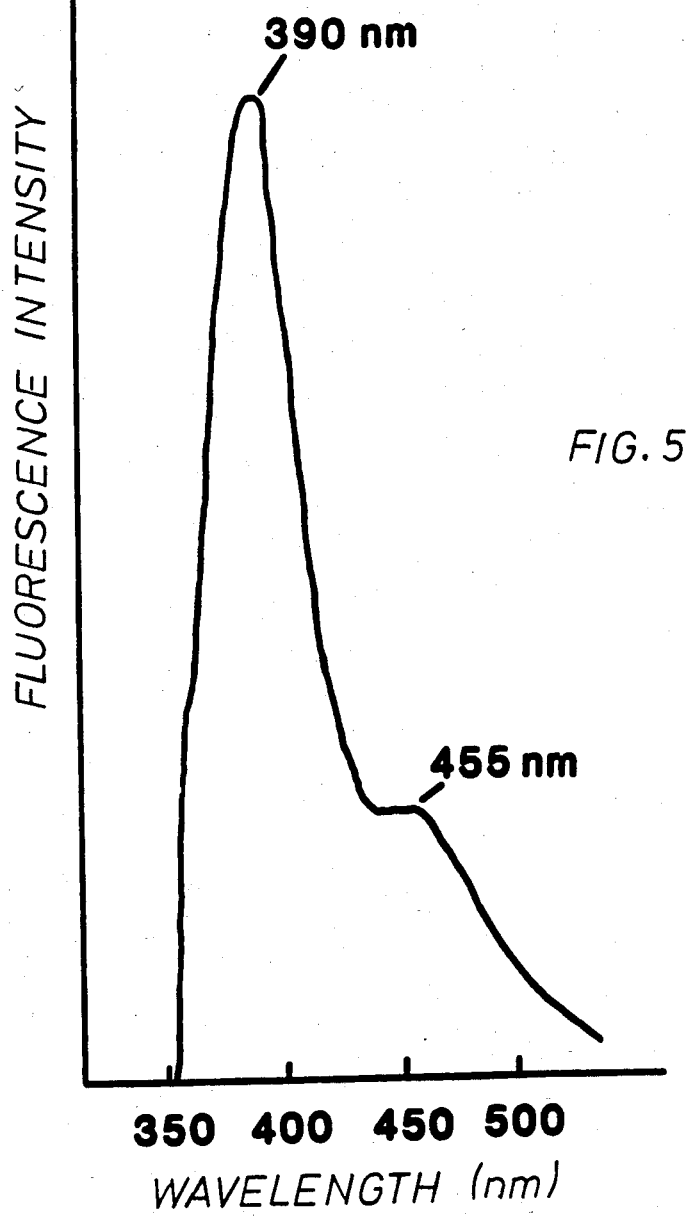
FIG. 5 is an emission spectrum for cartilage from chicken at an excitation of 340 nm.
Figure 6:
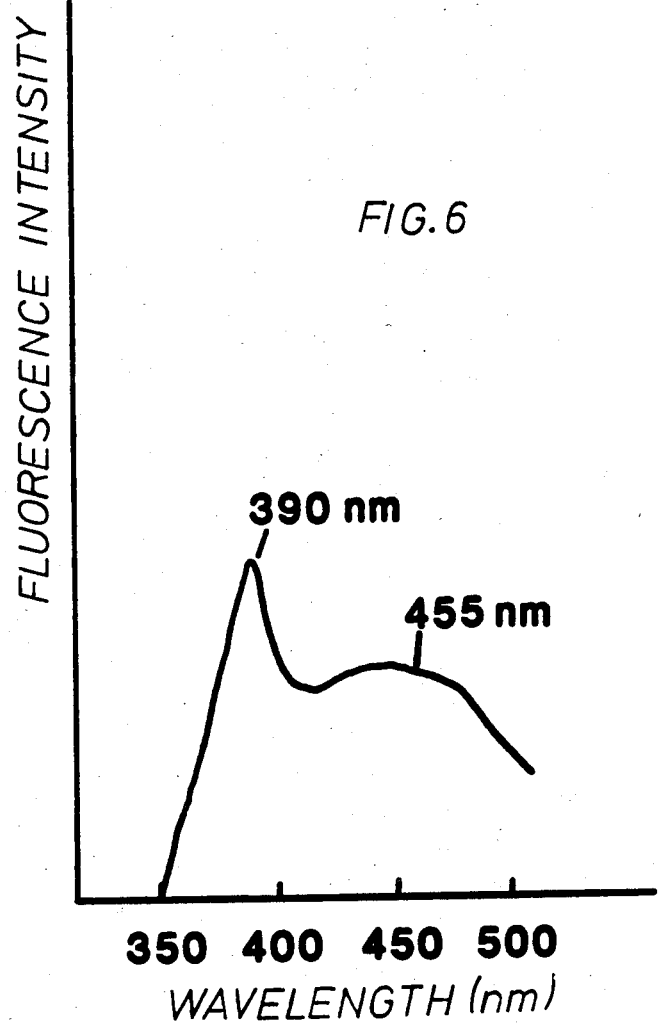
FIG. 6 is an emission spectrum for connective tissue from cow at an excitation of 340 nm.
Figure 7:
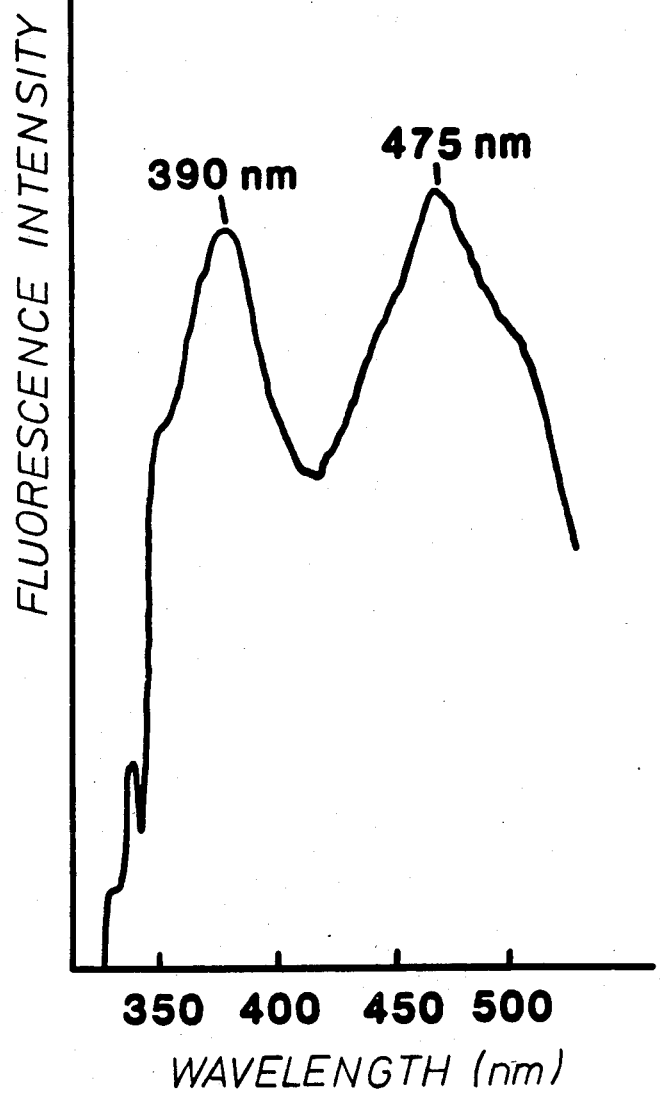
FIG. 7 is an emission spectrum for fat from cow at an excitation of 340 nm.

In order to investigate optimum emission and excitation wavelengths for the detection of bone, cartilage, connective tissue and fat in meat products (including poultry), bone, cartilage, connective tissue, fat and meat were studied in a spectrofluorometer. The excitation spectrum from bone, cartilage, connective tissue and fat had a peak at about 340 nm and the excitation limits were at about 325 nm and about 360 nm, which is illustrated in FIG. 3 by a measurement on cartilage from pig. At an irradiation of bone from pig, cow, lamb and chicken at about 340 nm, fluorescence emission spectra were caused with a peak at about 390 nm and a minor peak at about 455 nm, which is illustrated in FIG. 4 by a measurement on bone from pig. At an irradiation of cartilage from pig, cow and chicken at about 340 nm, fluorescence emission spectra were caused with a peak at about 390 nm and a minor peak at 455 nm, which is illustrated in FIG. 5 by a measurement on cartilage from chicken. At an irradiation of connective tissue at about 340 nm, a fluorescence emission spectrum was caused with a peak at about 390 nm and a minor peak at about 455 nm, which is illustrated in FIG. 6 by a measurement on connective tissue from cow. At an irradiation of fat from pig, cow and chicken at about 340 nm, fluorescence emission spectra were caused with a peak at about 390 nm and a peak at about 475 nm, which is illustrated in FIG. 7 by a measurement on fat from cow.

Figure 8:
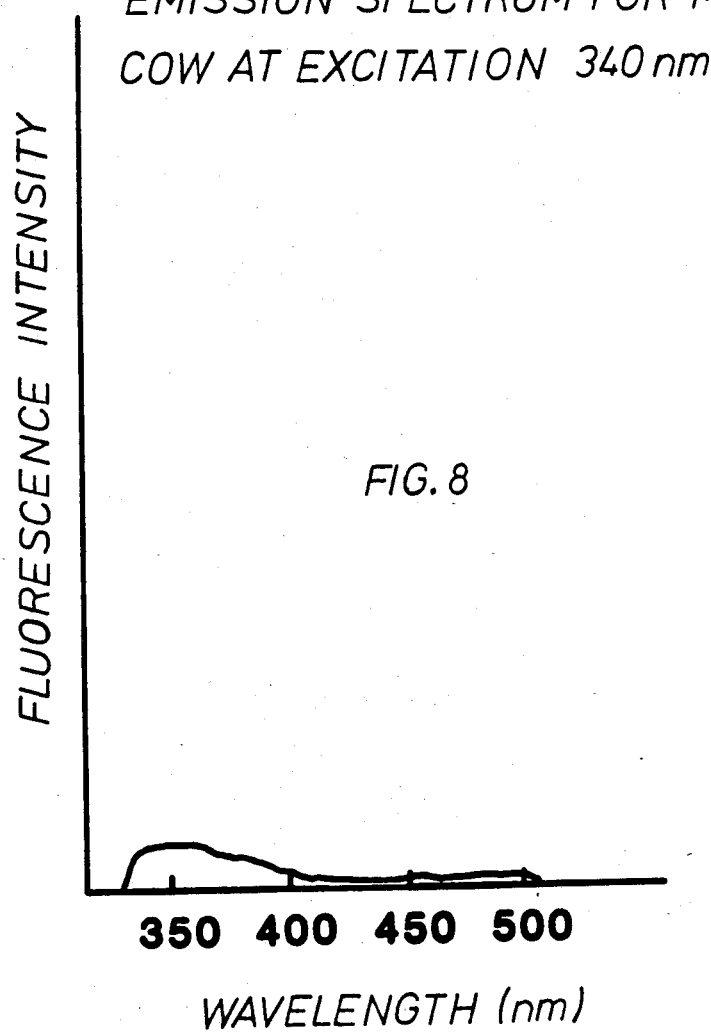
FIG. 8 is an emission spectrum for meat from cow at an excitation of 340 nm.

At an irradiation of meat from pig, cow and chicken at about 340 nm, no fluorescence was caused, which is illustrated in FIG. 8 by a measurement on meat from cow.

It can thus be established that electromagnetic radiation in the wavelength range of 325-360 nm unambiguously reveals the presence of any bone, cartilage, connective tissue and fat in meat products (including poultry) by the emission of characteristic fluorescence.

An apparatus for carrying out the method may include a screened box containing a source of radiation or a combination of radiation source and filter for emitting electromagnetic radiation in the range of about 325-360 nm, preferably with a peak at about 340 nm. The box further has one or more emission filters which transmit electromagnetic radiation in the range of about 365-490 nm, with peaks at 390 nm, 455 nm and 475 nm, the last two wavelengths being usable for distinguishing the detection of bone, cartilage, connective tissue from that of fat in meat. The box further has opening devices for inserting and extracting samples. For automatic instrument control, the apparatus may be provided with a photomultiplier or amplifier device with intensity threshold relays which are operably connected to a microprocessor. This permits obtaining a digital triggering for controlling a control mechanism having several alternative functions, such as expelling unacceptable products from a conveyor belt or indicating the purity of a fish or meat product in respect of the meat or flesh content, which can be directly printed on each package as consumer's information. Further, the undesired animal components can be detected by an optical system which is provided with said filter, and the detected image can be electronically transmitted via a TV equipment to an image analyser. A cutting and trimming machine can then be controlled from the image analyser on the basis of the image such that optimum trimming of the fish or meat product can be automatically obtained. The result of the image analysis is also convertible in a per se known manner into a quantitative determination, in the instant case of bone, cartilage and connective tissue, taken together, and/or of fat separately and of meat (muscles), the presence of which is determined quantitatively as a difference between the total area (volume) of the meat product in the field of vision and the sum of the areas (volumes) of bone, cartilage, connective tissue and fat. This type of quantitative determination may be inaccurate for thick or coarse meat products. If an accurate analysis is desirable, the quantitative analysis of such products is therefore preferably carried out with the aid of spectrofluorometry on a minced and suspended sample of the meat product.

Figure 9:
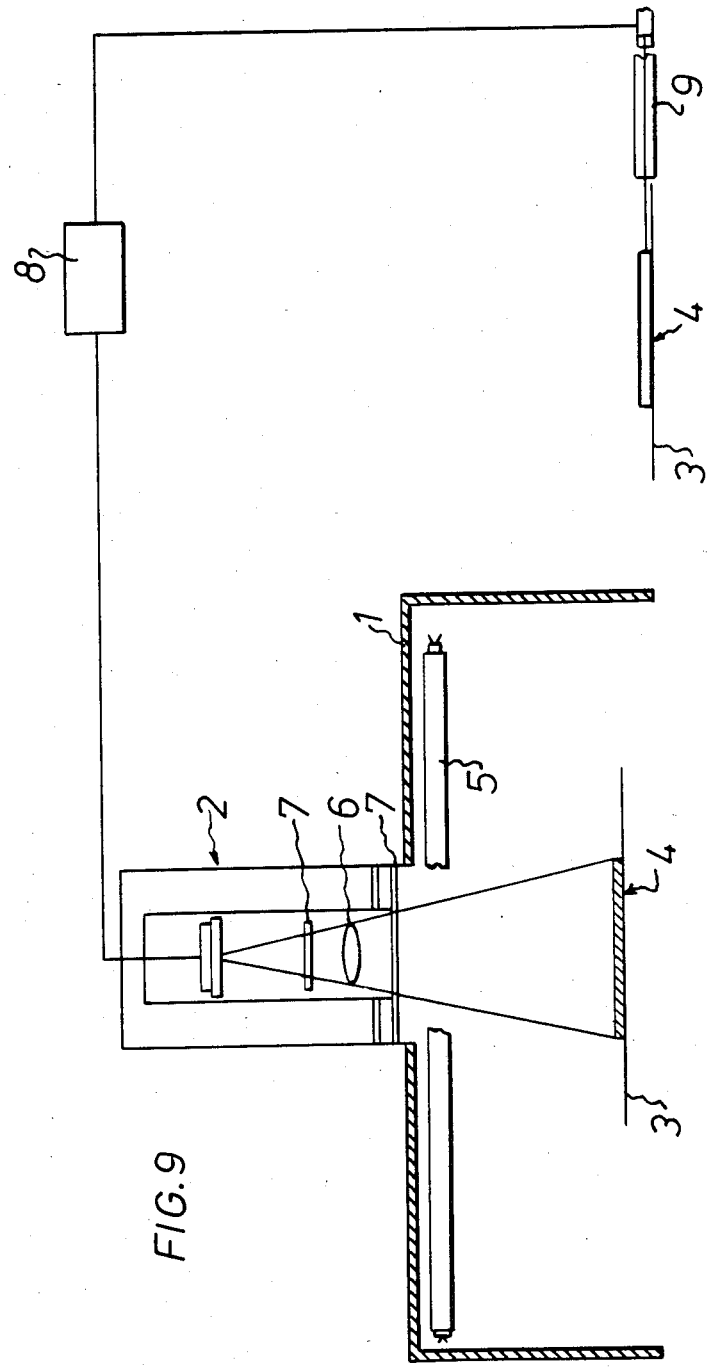
FIG. 9 schematically shows a system for carrying out the method according to the invention in a production/processing line.

FIG. 9 illustrates schematically a system for automatic fish fillet control in line downstream of a filleting machine not shown. The system comprises a U-shaped light box 1 and a detector 2, said light box straddling a conveyor belt 3 on which fillets 4 are advanced from the filleting machine for quality control. The light box 1 contains a light source 5 for 340 nm radiation which is so positioned in the box that its radiation impinges upon the fillets 4 successively advanced on the conveyor belt 3. Connected in series with the photodetector 2 which is connected to an aperture in the top of the box, are optics 6 and filters 7 for letting through 390 nm light which, by the excitation irradiation at 340 nm, has been emitted by a fillet containing bones. The detector 2 is sensitive to 390 nm light, and its output signal is proportional to the intensity of detected 390 nm light, which intensity in its turn is proportional to the amount of bones in the fillet. A signal processor 8 receives the output signal from the detector 2, and the output signal of the processor is used for activation of a piston-cylinder unit 9 which is disposed adjacent the conveyor belt 3 downstream of the light box 1 and ejects from the conveyor belt any fillet containing bones or unacceptably many bones, according to a threshold value setting in the signal processor.

What we claim and desire to secure by Letters Patent is:

1. A method for quality control of products from fish, meat, cattle, swine and poultry, for instance for controlling a process for treating or handling such products, characterised in that the product to be subjected to quality control, or a sample thereof, is exposed to excitation electromagnetic radiation within the range of about 325–360 nm, preferably about 340 nm, that any fluorescent radiation emitted by the product as a result of this irradiation, is analysed for identifying characteristic fluorescence from biological components in the product or a sample thereof, the presence of such biological components determining the quality of the product, and that said quality control is carried out in dependence upon the analysis result.

2. A method as claimed in claim 1 for quality control of fish products, characterised in that said analysis is carried out with emitted radiation in the wavelength range of about 365–450 nm for identification of characteristic fluorescence from fish bones.

3. A method as claimed in claim 2, characterised in that the said analysis is carried out with emitted radiation at 390 nm.

4. A method as claimed in claim 1 for quality control of meat products from cattle, swine and poultry, characterised in that said analysis is carried out with emitted radiation in the wavelength range of about 375–490 nm for identification of characteristic fluorescence from bones, cartilage, connective tissue and/or fat.

5. A method as claimed in claim 4, characterised in that said analysis is carried out with emitted radiation at 390 nm and/or 455 nm for identification of characteristic fluorescence from bones, cartilage and/or connective tissue.

6. A method as claimed in claim 4, characterised in that said analysis is carried out with emitted radiation at 390 nm and/or 475 nm for identification of characteristic fluorescence from fat.

7. A method as claimed in any one of claims 4–6, characterised in that said analysis comprises a quantity determination of bones, cartilage, connective tissue taken together and/or of fat and, via these quantity determinations, of meat, said quantity determination being carried out by means of fluorescent image analysis or spectrofluorometry or by means of a photodetector on whole or minced products.

8. A method as claimed in claim 7, the products to be subjected to quality control being carried on a conveyor past a quality determining instrument, characterised in that the analysis result is used for controlling a device for removing qualitatively unacceptable products from said conveyor.

9. A method for assaying for fish bone in edible fish flesh containing fish bone, said method comprising
exposing fish flesh to excitation electromagnetic radiation having a wavelength of about 325 nm to about 355 nm to produce fluorescent radiation from said flesh; and
sensing the fluorescent radiation having a wavelength of about 365 nm to about 450 nm characteristic of fish bone in said flesh.

10. Method according to claim 9 wherein the excitation electromagnetic radiation has a wavelength of about 340 nm.

11. Method according to claim 10 wherein the emitted radiation has a wavelength of about 390 nm.

12. Method according to claim 9 wherein the fish flesh is minced.

13. Method according to claim 9 wherein the fish flesh is a cod fillet.

14. A method for assaying for non-nutritional components selected from the group consisting of bone, cartilage, connective tissue or fat in edible flesh containing at least one of said components from an animal selected from the group consisting of pig, cow, lamb and chicken, said method comprising:
exposing the flesh to excitation electromagnetic radiation having a wavelength of about 325 nm to about 360 nm to produce fluorescent radiation from said flesh; and
sensing the fluorescent radiation having a wavelength of about 390 nm or about 455 nm characteristic of said non-nutritional component.

15. Method according to claim 14 wherein the excitation electromagnetic radiation has a wavelength of about 340 nm.

16. Method according to claim 15 wherein the emitted radiation has wavelengths of about 390 nm and about 455 nm and radiation of both wavelengths is detected.

17. Method according to claim 14 wherein the flesh is minced.

18. A method for assaying for fat in flesh from a pig, cow or chicken containing fat, said method comprising
exposing the flesh to excitation electromagnetic radiation having a wavelength of about 325 nm to about 355 nm to produce fluorescent radiation from said flesh; and
sensing the fluorescent radiation having a wavelength of about 390 nm or about 475 nm characteristic of fat in said flesh.

19. Method according to claim 18 wherein the excitation electromagnetic radiation has a wavelength of about 340 nm.

20. Method according to claim 19 wherein the emitted radiation has wavelengths of about 390 nm and about 475 nm and radiation of both wavelengths is detected.

21. Method according to claim 18 wherein the flesh is minced.

22. A method for assaying edible flesh from an animal selected from the group consisting of pig, cow and chicken, said flesh containing fat and at least one non-nutritional component selected from the group consisting of bone, cartilage and connective tissue, said method comprising exposing the flesh to excitation electromagnetic radiation having a wavelength of about 325 nm to about 360 nm to produce fluorescent radiation from said flesh;

sensing the fluorescent radiation having a wavelength of about 390 nm and about 475 nm characteristic of fat in said flesh; and sensing the flourescent radiation having a wavelength of about 390 nm and about 455 nm characteristic of non-nutritional components in said flesh.

23. Method according to claim 22 wherein the excitation electromagnetic radiation has a wavelength of about 340 nm.

* * * * *